United States Patent [19]

Mellul et al.

[11] Patent Number: 5,358,719
[45] Date of Patent: Oct. 25, 1994

[54] POROUS MICROSPHERES COATED WITH A PERFLUORINATED OIL, A FLUORINATED SILICONE OIL OR A SILICONE GUM AND COSMETIC COMPOSITIONS CONTAINING THEM

[75] Inventors: Myriam Mellul, L'Hay les Roses; Pascal Arnaud, Paris, both of France

[73] Assignee: L'Oreal, Paris, France

[21] Appl. No.: 871,799

[22] Filed: Apr. 21, 1992

[30] Foreign Application Priority Data

Apr. 22, 1991 [FR] France ................... 91 04932

[51] Int. Cl.$^5$ .................. A61K 7/02; A61K 7/027; A61K 7/035
[52] U.S. Cl. .................. 424/497; 424/401; 424/63; 424/64
[58] Field of Search ................ 424/401, 63, 64, 497; 428/391, 405

[56] References Cited

U.S. PATENT DOCUMENTS

| | | | |
|---|---|---|---|
| 4,917,930 | 4/1990 | McCormick | 424/501 |
| 5,035,885 | 7/1991 | Arraudeau et al. | 424/501 |
| 5,035,886 | 7/1991 | Chakrabarti et al. | 424/401 |

FOREIGN PATENT DOCUMENTS

| | | |
|---|---|---|
| 0212870 | 3/1987 | European Pat. Off. . |
| 0254612 | 1/1988 | European Pat. Off. . |
| 0340103 | 11/1989 | European Pat. Off. . |
| 0379409 | 7/1990 | European Pat. Off. . |
| 0390206 | 10/1990 | European Pat. Off. . |
| 0407089 | 1/1991 | European Pat. Off. . |
| 0422984 | 4/1991 | European Pat. Off. . |
| 2151170 | 4/1973 | France . |
| 2530250 | 1/1984 | France . |
| 8801164 | 2/1988 | PCT Int'l Appl. . |
| 8910132 | 11/1989 | PCT Int'l Appl. . |

OTHER PUBLICATIONS

French Search Report of FR 91 04932.

*Primary Examiner*—Thurman K. Page
*Assistant Examiner*—Peter F. Kulkosky
*Attorney, Agent, or Firm*—Cushman, Darby & Cushman

[57] ABSTRACT

Porous microspheres have fixed on the exterior surface thereof a coating of at least one of a perfluorinated oil, a fluorinated silicone oil or a silicone gum. The pores of the microspheres can be charged with a hydrophilic, lipophilic or perfluorinated phase. The microspheres are employed in cosmetic compositions.

19 Claims, No Drawings

POROUS MICROSPHERES COATED WITH A PERFLUORINATED OIL, A FLUORINATED SILICONE OIL OR A SILICONE GUM AND COSMETIC COMPOSITIONS CONTAINING THEM

The present invention relates to porous microspheres with a perfluorinated oil, a fluorinated silicone oil or silicone gum and their use in cosmetic compositions, particularly in lip rouges, powders, eyelid and cheek makeup compositions, mascaras, complexion foundations, creams, lotions, serums and deodorants.

It is well known that perfluorinated oils, in particular, perfluoropolyethers produce particularly interesting cosmetic properties. However, their use has been considerably limited because of their insolubility in the aqueous phase as well as in conventional oils and silicone oils.

To resolve this problem, attempts have been made to incorporate them in cosmetic compositions either in the form of a dispersion, as for example, in lip rouges, compact powders, cheek makeup compositions, oil-in-water emulsions or water-in-oil emulsions or even in aqueous gels as described in EP patent 196 904, or in the form of an emulsion in the presence of a surfactant, in glycerol or in a concentrated aqueous solution of a polyol having a functionality greater than 3 such as, for example, sorbitol as described in EP patent 390 206.

To a lesser degree, the incorporation problem is also associated with fluorinated silicone oils and silicone gums which are only soluble in silicone oils. Dispersions in an anhydrous phase do not permit a very high amount of incorporation, in the measure where the affinity of droplets of perfluorinated oils, fluorinated silicones or even silicone gums for the matrix, are weak and can produce brittleness of the matrix structure as is the case for lip rouges.

On the other hand, introduction in emulsified form or in dispersion in an aqueous gel permits to increase the concentration but requires in the case an emulsion, the use of a surfactant and in the case of a dispersion, a certain viscosity.

After significant research and in a surprising manner, the applicants have noted that the problem of introducing larger amounts of perfluorinated oil, fluorinated silicone and silicone gum, could be resolved without using a surfactant, and without having viscosity constraints.

According to the invention, the solution to the problem comprises using porous microspheres previously coated with a perfluorinated oil, a fluorinated silicone or a silicone gum.

Such porous microspheres thus coated exhibit excellent cosmetic properties which, until now, could not be obtained in accordance with the described prior techniques.

The present invention thus relates to porous microspheres coated with a perfluorinated oil, a fluorinated silicone or a silicone gum, the coating being fixed on the external surface of the said microspheres.

The coating substance, as will be better defined below, is of a nature such that it does not penetrate the interior of the pores of the microspheres and is fixed only on the exterior thereof.

The porous microspheres exhibit an average particle size lower than 800 $\mu$m and preferably between 0.1 and 300 $\mu$m. These microspheres are in spheric or spheroidal form and have a network of interconnected and open pores on the exterior and are optionally capable of being filled with a hydrophilic or lipophilic liquid phase according to their chemical nature.

Among the porous microspheres which can be employed in accordance with the invention mention can be made of:

polyamides such as crosslinked poly $\beta$-alanine described in French patents 83 11609 and 87 17573, polyacrylates such as POLYTRAP Q5-6603 sold by Dow Corning, polyamides such as ORGASOL sold by Atochem, polymethacrylates, such as MICROPEARL M, sold by Seppic or PLASTIC POWDER A sold by Nikkol, styrene-divinylbenzene copolymers such as those sold by APS or PLASTIC POWDER FP sold by Nikkol, polyethylenes and polypropylenes, such as ACCUREL EP400 sold by Akzo, celluloses, such as MICROSPHERICAL CELLULOSE, sold by Chisso, silicones, such as SILICONE POWDER X2-1605, sold by Dow Corning, silicas, such as SILCRON G640, sold by SCM, and hydroxyapatite powders, such as CERAPOL, sold by Koken.

In accordance with the invention, the coating of the porous microspheres is generally effected by using from 0.1 to 500 weight percent, and preferably from 1 to 300 weight percent of perfluorinated oil, fluorinated silicone oil, or silicone gum, relative to the weight of the microspheres.

Among the perfluorinated oils usable in accordance with the invention, mention can principally be made of those having viscosities generally less than $5 \times 10^{-3}$ $m^2/s$ at 20° C. Principally among these oils are the following:

perfluoroalkanes having the general formula: $C_nF_{2n+2}$ wherein $n > 19$ and perfluoropolyethers having the following general formulas:

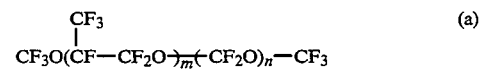
(a)

wherein the ratio m/n is 5 to 40,

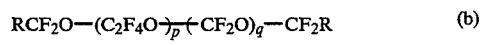
(b)

wherein the ratio p/q is equal to 0.5 to 1.5,

R represents a fluorine atom, —COOH, —COOCH$_3$, —CH$_2$OH, —CH$_2$O—CH$_2$—CHOH—CH$_2$OH or —CH$_2$(OCH$_2$CH$_2$)$_p$—OH wherein p is 1 or 2,

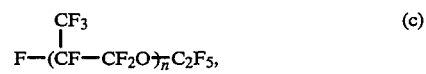
(c)

wherein n is equal to 10–500, and

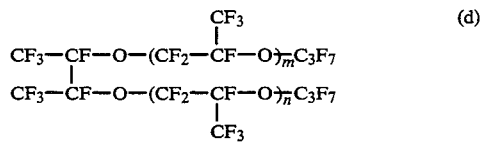
(d)

wherein m and n are whole numbers ranging from 0 to 3, such that the molecular weight is greater than 1,000.

Among the fluorinated silicone oils, mention can principally be made of those having a viscosity between $1 \times 10^{-4}$ and $1 \times 10^{-2}$ m²/s at 25° C. and having the following formulas:

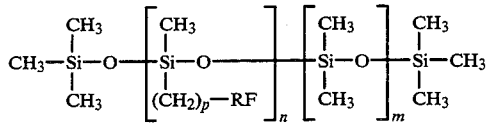

(a)

wherein
n is a whole number ranging from 1 to 300,
m is a whole number ranging from 0 to 150,
p is a whole number ranging from 0 to 5, and
RF is a perfluoroalkyl radical having from 1 to 8 carbon atoms, and

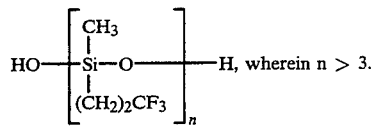

(b)

Finally, among the silicone gums, mention can be made of those having viscosities greater than or equal to $1 \times 10^{-2}$ m²/s at 25° C. and preferably greater than or equal to $5 \times 10^{-2}$ m²/s at 25° C.

Among these silicone gums mention can principally be made of those corresponding to the following general formula:

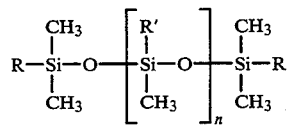

wherein
R represents, —CH₃, OH or —CH=CH₂,
R' represents —CH₃ or —C₆H₅ and
n is such that the viscosity is $>1 \times 10^{-2}$ m²/s at 25° C.

Among the perfluorinated oils and in particular among the perfluoropolyethers having the formulas given above, mention can principally be made of the products sold by Montefluos under the following tradenames: FOMBLIN HCO4, FOMBLIN HC25, FOMBLIN HCR, FOMBLIN Z03, FOMBLIN Z15, FOMBLIN Z25, FOMBLIN Z60, FOMBLIN ZDEAL, FOMBLIN ZDIAC, FOMBLIN ZDOL, FOMBLIN ZTETRAOL AND FOMBLIN ZDOL TX, the product sold by du Pont de Nemours under the tradename KRYTOX and the product sold by Hoechst under the tradename HOSTINERT.

Among the silicone oils responding to the formulas given above, mention can be made of the products sold by Shinetsu under the tradenames X22819, X22820, X22821 and X22822 as well as those under the tradenames FL100 ($4.5 \times 10^{-4}$ m²/s), FL100 ($1 \times 10^{-3}$ m²/s) and FL100 ($1 \times 10^{-2}$ m²/s), the products sold by Dow Corning under the tradename FS 1265 and that sold by General Electric under the tradename FF150.

Among the silicone gums, mention can principally be made of the dimethicone sold by Wacker under the tradename AK500000 and the dimethiconol sold under the tradename SGM3 by Dow Corning.

When the microspheres are coated with perfluorinated oils or fluorinated silicone oils their formulation requires heating in the presence of an oily phase as is the case with lip rouges, cheek makeup or emulsions, and there will be used a coating phase containing, preferably, at least 10 weight percent pefluorinated oils or fluorinated silicone oils having polar functions such as (a) $RCF_2(OCF_2-CF_2)_p-(OCF_2)_q-_{OCF2}R$
wherein
the ratio p/q is 0.5 to 1.5 and
R represents —COOH or —CH₂O—CH₂—CHOH—CH₂OH, and

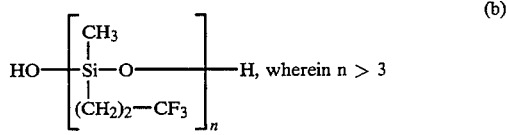

(b)

in order to increase the interactions of the coating phase with the porous microspheres.

According to a preferred embodiment of the invention, the porous microsphere prior to being coated are charged at the interior of the pores with a hydrophilic, lipophilic or perfluorinated phase. However, it is not required that this phase be miscible vis-a-vis the coating substance and preferably is not miscible vis-a-vis the dispersion medium. According to this embodiment, a stable dispersion of three phases non-miscible among themselves can be produced without using a surfactant.

It is appropriate, moreover, to note that the presence of a charging phase permits to increase the amount of coating phase.

According to this embodiment, the hydrophilic phase can be water, a polyhydroxyl alcohol or a mixture thereof such as, for example, a mixture of water and glycerol or 1,2-propanediol in amounts ranging from 0.1 to 10 times the mass of porous microspheres and preferably between 0.1 and 5 times.

This hydrophilic phase can include hydrosoluble active components which are generally employed in cosmetic or pharmaceutical compositions, and in particular, hydrating agents such as D-panthenol, glyceryl polymethacrylate, glyceryl, sodium hyaluronate, the sodium salt of pyroglutamic acid and vitamins.

Among the substances capable of constituting the lipophilic phase, mention can principally be made of known oils conventionally employed in cosmetics such as mineral oils including paraffin oil, vegetable oils such as jojoba oil or ricin oil, animal oils such as squalene or even synthetic oils such as isopropyl myristate, silicone oils or fluorinated oils as well as, moreover, essential oils or perfume extracts, in amounts ranging from 0.1 to 5 times the mass of the porous microspheres and preferably from 0.1 to 3 times.

The lipophilic phase can, however, also serve as a vehicle for a cosmetically or pharmaceutically liposoluble active substance, in particular, α-tocopherol acetate, tocopherol nicotinate, β-carotene, N,N-diethyltoluamide, liposoluble U.V. filters, zinc ricinoleate, antioxidants, preservatives and the like.

When the microspheres are charged with a perfluorinated phase, it is a question of a perfluorinated oil having a molecular mass lower than 1,000 and preferably lower than 500.

Among these perfluorinated oils, mention can be made of the following:

(1) those belonging to the group of perfluoroalkanes, perfluorocycloalkanes, perfluoropolycycloalkanes and perfluoro (alkylcycloalkanes);

as examples of perfluoroalkanes, mention can be made of the series of linear alkanes, such as perfluorocyclooctane, perfluorononane or even perfluorodecane;

as examples of perfluorocycloalkanes and perfluor(alkyl cylcoalkanes), mention can be made of perfluorodecaline, perfluoro (methyldecaline), perfluoro ($C_3$–$C_5$-alkylcylcohexanes) such as perfluoro (butylcyclohexane), derivatives of bicyclo[3,3,1] nonane, such as trimethylbicyclo[3,3,1] nonane, perfluorinated derivatives of adamantane, such as perfluorodimethyl adamantane and perfluorotetradecahydrophenanthrene;

(2) those belonging to the group of aromatic perfluorinated hydrocarbons (perfluoroarenes), as the perfluorinated derivatives of naphthalene such as perfluoronaphthalene and perfluoromethyi-1-naphthalene;

(3) those belonging to the group of perfluorinated hydrocarbons containing at least one heteroatom, for example, perfluorinated tertiary amines, such as perfluorotributylamine, or saturated heterocyclic compounds, substituted by alkyl groups, as perfluoro (alkyltetrahydropyrans), such as perfluoro (hexyltetrahydropyran), perfluoro (alkyltetrahydrofuran), such as perfluoro (heptyltetrahydrofuran) and perfluoro (butyltetrahydrofuran) or morpholine derivatives, such as perfluoro (N-pentylmorpholine); and (4) those belonging to the group of low molecular mass perfluoro-polyethers such as, for example, products sold by Montefluos under the tradename GALDEN, in particular GALDEN D02 and GALDEN D03.

In accordance with this embodiment, the coating of the charged porous microspheres is generally effected using from 0.1 to 500 weight percent and preferably from 1 to 300 weight percent of a perfluorinated oil, a fluorinated silicone oil or a silicone gum, relative to the weight of the microspheres, this amount varying according to the nature of the coating material.

The present invention also relates to various procedures for preparing the coated porous microspheres.

According to a first process, there are mixed, in a suitable container, with stirring, porous microspheres with the coating substance in the liquid state. This process is applicable essentially to perfluorinated oils and to fluorinated silicone oils.

Another process, preferentially employed when using silicone gums, comprises effecting the coating in a solvent in which the silicone gum has previously been dissolved and then evaporating the solvent to effect the coating.

The present invention also relates to a process for preparing charged and coated microspheres.

The charging and coating can be effected separately or simultaneously according to various procedures.

The most simple process comprises mixing in an appropriate container with stirring the porous microspheres with the hydrophilic or lipophilic charging substance, then adding, after return to the pulverulent state, the coating substance in the liquid state. This process is applicable essentially to perfluorinated oils and to fluorinated silicone oils.

When the coating substance is dispersible in the charging substance, as is the case for perfluorinated oils and fluorinated silicone oils in polyhydroxyl alcohols such as glycerol or mixtures of water and a polyhydroxyl alcohol such as sorbitol, the charging and coating can be effected simultaneously according to the preceding process, by mixing the microspheres and the dispersion.

Another process preferentially employed for silicone gums comprises effecting the charging and the coating in a suitably selected solvent.

In accordance with this process, the solvent must in effect satisfy certain conditions:

its boiling temperature must be the lowest possible and lower than that of the hydrophilic, lipophilic or perfluorinated substance, it must not form a significant azeotrope with the charging substance, its affinity vis-a-vis the microspheres must be negligible with respect to that of the charging substance, and finally is must be little or non-toxic.

Among the particularly appropriate solvents for use in the process, mention can principally be made of diethyl ether, dichloromethane and n-hexane.

In accordance with this process, there are introduced into the solvent the microspheres, the hydrophilic, lipophilic or perfluorinated charging substance which is found in the dispersed or dissolved state depending on its solubility and the charging is effected by manual or mechanical stirring or by evaporating the solvent when the charging substance is in solution.

To the preceding system there is then added a solution or a dispersion of the coating substance in the solvent that is then evaporated in order to coat the charged microspheres.

It is noted that the charging step can be effected in a solvent in the presence of the coating substance, dissolved or dispersed, on the condition that the affinity of the charging substance for the microspheres is greater than that of the coating substance.

It is particularly advantageous to carry out the charging step in a solvent because this process permits effecting chargings which are impossible or very difficult by direct mixing. Consequently, microspheres are obtained which are charged in a more homogeneous fashion. This process also favors the penetration of the charging substances at the interior of the pores, which is manifested by a powdery charged product the particles of which are well separated, and contain an optimum amount of the charge in the microspheres which is greater than that obtained by direct mixing.

The coated microspheres, or charged and coated microspheres, are provided in the form of a product having a powdery consistency which is then dispersed in a continuous phase which is non-miscible vis-a-vis the coating substance and also preferably non-miscible vis-a-vis the charging substance. This continuous phase can be a cosmetic or pharmaceutical vehicle which can be an aqueous solution of the lotion, gel, oil-in-water emulsion or water-in-oil emulsion type, an anhydrous phase in the sense of lip rouges, or binders employed in powders or eyelid or cheek makeup formulations.

In the cosmetic compositions according to the invention the amount of coated microspheres or optionally charged and coated microspheres can vary within wide limits but the amount is generally between 0.1 and 60 weight percent and preferably between 4 and 20 weight percent in cosmetic makeup compositions.

As an illustration and without any limiting character several examples of preparing coated microspheres and charged and coated microspheres, as well as examples of cosmetic composition containing such microspheres are now given.

Preparation of Microspheres

I. Preparation of coated microspheres

EXAMPLE 1

To 10 g of crosslinked poly β-alanine microspheres, in the dry state, 10 g of perfluorinated oil sold under the tradename FOMBLIN HC25 by Montefluos are introduced.

The mixture is stirred using a Rayneri stirrer fitted with a deflocculator until a homogeneous mixture is produced.

A pulverulent product is obtained which is easily dispersible in an oily or siliconed phase.

II. Preparation of charged and coated microspheres

EXAMPLE 2

To 10 g of crosslinked poly β-alanine microspheres, in the dry state, 20 g of water are added, so as to obtain 30 g of hydrated microspheres, 10 g of perfluorinated oil, sold under the tradename FOMBLIN HC25 by Montefluos, are then introduced.

The mixture is stirred using a Rayneri agitator fitted with a deflocculator until a homogenous mixture is obtained.

EXAMPLE 3

10 g of crosslinked poly B-alanine microspheres are charged with 20 g of glycerol. 10 g of perfluorinated oil, sold under the tradename FOMBLIN HC25 by Montefluos, are then added. The mixture is stirred using a Rayneri stirrer fitter with a deflocculator until a homogeneous mixture is obtained.

A pulverulent product is obtained which is easily dispersible in an oily or siliconed phase.

EXAMPLE 4

2 g of perfluorinated oil, sold under the tradename FOMBLIN Z TETRAOL by Montefluos, are mixed with 8 g of perfluorinated oil, sold under the tradename FOMBLIN HC25 by Montefluos.

This mixture is then dispersed in 20 g of glycerol and the whole is introduced with 10 g of crosslinked poly β-alanine microspheres, in the dry state, in a suitable container.

The whole is stirred using a Rayneri stirrer fitted with a deflocculator while slightly heating until there is obtained a homogeneous, pulverulent product which is easily dispersible in an oily or siliconed phase.

EXAMPLE 5

To 10 g of crosslinked poly β-alanine microspheres, in the dry state, there are added 30 g of a dispersion containing 10 g of perfluorinated oil, sold under the tradename FOMBLIN Z60 by Montefluos, in 20 g of a solution constituted by 5 g of D-panthenol in 15 g of glycerol. The whole is stirred using Rayneri stirrer fitted with a deflocculator until a homogeneous, pulverulent product is obtained which is easily dispersible in an oily or siliconed phase.

EXAMPLE 6

10 g of microspheres, sold under the tradename POLYTRAP Q5-6603 by Dow Corning, are introudced into a reactor and heated to 70° C. 15 g of α-tocopherol acetate, previously heated under nitrogen to 70° C., are added.

The whole is stirred under nitrogen until a homogeneous product is obtained, 15 g of perfluorinated oil, sold under the tradename FOMBLIN HC25 by Montefluos, are then added.

After homogenization a pulverulent product is obtained which is easily dispersible in a hydrophilic phase.

EXAMPLE 7

To 10 g of silicone microspheres, sold under the tradename SILICONE POWDER X2-1605 by Dow Corning, there are added 10 g of silicone oil, sold under the tradename DC FLUID 200 ($0.1 \times 10^{-4}$ m$^2$/s) by Dow Corning.

The whole is stirred using a Rayneri stirrer fitted with a deflocculator until a pulverulent product is obtained. 5 g of perfluorinated oil, sold under the tradename FOMBLIN HC25 by Montefluos, are then added.

This mixture is again stirred under the same conditions as before, and a powdery product is obtained which is easily dispersible in a hydrophilic phase.

EXAMPLE 8

To 10 g of silica microspheres, sold under the tradename SILCRON G640 by Chimilab, a distributor of SCM, there are added 30 g of a dispersion constituted of 10 g of perfluorinated oil, sold under the tradename FOMBLIN HC25 by Montefluos, in 20 g of glycerol.

The whole is stirred using a Rayneri stirrer fitted with a deflocculator while slightly heating until a pulverulent product is obtained which is easily dispersible in an oily or siliconed phase.

EXAMPLE 9

To 10 g of crosslinked poly β-alanine microspheres, in the dry state, there are added 30 g of a dispersion constituted of 10 g of fluorinated silicone oil, sold under the tradename FL100 ($1 \times 10^{-3}$ m$^2$/s) by Shinetsu, in 20 g of glycerol.

The whole is stirred using a Rayneri stirrer fitted with a deflocculator while heating slightly until a homogenous mixture is obtained. A pulverulent product is obtained which is easily dispersible in an oily phase.

EXAMPLE 10

10 g of microspheres, sold under the tradename POLYTRAP Q5-6603 by Dow Corning, are introduced in a reactor and heated to 70° C. 15 g of α-tocopherol acetate, previously heated under nitrogen to 70° C., are then added. The whole is stirred under nitrogen until a homogeneous product is obtained. 15 g of fluorinated silicone oil sold under the tradename FL100 ($4.5 \times 10^{-4}$ m$^2$/s) by Shinetsu, are then added.

After homogenization, a pulverulent product is obtained which is easily dispersible in a hydrophilic phase.

EXAMPLE 11

10 g of crosslinked poly β-alanine, in the dry state, and 30 g of a 50:50 mixture of water and glycerol are dispersed in 150 cm$^3$ of n-hexane. A solution of 5 g of silicone gum, sold under the tradename SGM-3 by Dow Corning in 100 cm$^3$ of n-hexane, are then added.

The whole is stirred until the droplets of the hydrophilic phase disappear. The solvent is then evaporated under a vacuum at ambient temperature with a rotary evaporator. After complete removal of the solvent, a product is obtained which becomes pulverulent again after a slight grinding. This product is then easily dispersible in an oily phase.

EXAMPLE 12

To 10 g of cellulose microspheres, sold by Chisso, 10 g of glycerol are added. The whole is stirred using a Rayneri stirrer fitted with a deflocculator while slightly heating until a homogeneous mixture is obtained. The microspheres, thus swollen, are dispersed in 150 cm$^3$ of n-hexane. A solution of 5 g of silicone gum, sold under the tradename SGM-3 by Dow Corning, in 100 cm$^3$ of n-hexane is added. All the solvent is then evaporated with a rotary evaporator under a vacuum at ambient temperature so as to effect the coating.

A product is obtained which becomes pulverulent again after a slight grinding. This product is easily dispersible in an oil phase.

EXAMPLE 13

10 g of microspheres, sold under the tradename POLYTRAP Q5-6603 by Dow Corning, are dispersed in 150 cm$^3$ of dichloromethane. A solution of 15 g of α-tocopherol acetate and 5 g of silicone gum, sold under the tradename SGM-3 by Dow Corning in 100 cm$^3$ of dichloromethane, is then added. All the solvent is then evaporated with a rotary evaporator under a vacuum at ambient temperature. A product is obtained which becomes pulverulent again after a slight grinding. The product is easily dispersible in a hydrophilic phase.

EXAMPLE 14

To 10 g of microspheres, sold under the tradename POLYTRAP Q5-6603 by Dow Corning, there are added 20 g of perfluorotributylamine, sold under the tradename FLUORINERT FC-43 by 3M. The whole is stirred using a Rayneri stirrer fitted with a deflocculator until a homogeneous mixture is obtained.

The microspheres, thus swollen, are dispersed in 150 cm$^3$ of n-hexane. A solution of 5 g of silicone gum, sold under the tradename SGM-3 by Dow Corning, in 100 cm$^3$ of n-hexane is then added. All the solvent is evaporated using a rotary evaporator under a vacuum at ambient temperature thus effecting the coating.

A product is obtained which becomes pulverulent again after a slight grinding. The product is easily dispersible in an aqueous or oily phase.

Examples of Cosmetic Compositions

EXAMPLE 15

Lip rouge

| | |
|---|---|
| Poly β-alanine microspheres charged and coated, obtained according to Example 4 | 4 g |
| Ozokerite | 14.4 g |
| Microcrystalline wax | 4.8 g |
| Candelilla wax | 7.2 g |
| Jojoba oil | 6.0 g |
| Ricin oil | 1.2 g |
| Liquid lanolin | 18.0 g |
| Acetylated lanolin | 9.6 g |
| Petrolatum oil | 10.8 g |
| Talc | 3.6 g |
| Mica-titanium | 8.4 g |
| D&C Red 7 calcium lake | 5.04 g |
| D&C Red 7 barium lake | 2.76 g |
| FDC yellow 5 | 0.96 g |
| Titanium dioxide | 3.0 g |
| Butylhydroxy toluene | 3.0 g |
| Perfume, sufficient amount | |

The charged and coated microspheres are introduced last in a lip rouge base melted at 90° C. The dispersion of these microspheres is very rapid, thereby permitting very easy incorporation and dispersion of the coating fluorinated oils. This is not the case when these fluorinated oils are introduced directly in the base.

After casting and cooling sticks are obtained which are homogeneous, unctuous, very smooth and slippery on application. They produce a very brilliant film on the lips and have hydrating properties.

EXAMPLE 16

Lip rouge

| | |
|---|---|
| Charged and coated poly β-alanine microspheres, obtained according to Example 11 | 4.5 g |
| Ozokerite | 14.33 g |
| Microcrystalline wax | 4.78 g |
| Candelilla wax | 7.16 g |
| Jojoba oil | 5.97 g |
| Ricin oil | 1.19 g |
| Liquid lanolin | 17.91 g |
| Acetylated lanolin | 9.55 g |
| Petrolatum oil | 10.75 g |
| Talc | 3.58 g |
| Mica titanium | 8.36 g |
| D&C Red 7 calcium lake | 5.01 g |
| D&C Red barium lake | 2.74 g |
| FDC Yellow 5 | 0.96 g |
| Titanium dioxide | 2.98 g |
| Butylhydroxytoluene | 0.23 g |
| Perfume, sufficient amount | |

The charged and coated microspheres are introduced last in the lip rouge base melted at 80–85° C. The dispersion of these microspheres is very rapid thus permitting a very easy incorporation and dispersion of the coating silicone gum. This is impossible when this gum is introduced directly in this base which does not contain silicone oil.

EXAMPLE 17

Eyelid makeup

| | |
|---|---|
| Charged and coated poly β-alanine microspheres, according to Example 3 | 4 g |
| Pigments | 30.0 g |
| Mica titanium | 50.0 g |
| Liquid lanolin | 5.0 g |
| Petrolatum oil | 4.8 g |
| Propyl parahydroxybenzoate | 0.2 g |
| Talc, sufficient amount for | 100.0 g |

The resulting eyelid makeup is smooth and has good covering power.

EXAMPLE 18

Gel

| | |
|---|---|
| Charged and coated POLYTRAP Q5-6603 microspheres obtained according Example 6 | 3.5 g |
| Carbopol 941 | 0.50 g |
| Triethanolamine, sufficient for pH = 6 | |
| Water, sufficient amount for | 100. g |

The charged and coated microspheres are dispersed before neutralization by triethanolamine when the viscosity of the system is still low. This permits to maintain, during gelification, a good state of dispersion of the microspheres and consequently the perfluorinated oil of the coating. This is difficult to effect by direct introduction of perfluorinated oil in the gel.

EXAMPLE 19

Composition of the "oil-free" type

| (A) | charged and coated POLYTRAP Q5-6603 microspheres obtained according to Example 6 | 4 g |
|---|---|---|
|  | Carbopol 940 | 0.58 g |
| (B) | Carbopol EX 183 | 0.10 g |
|  | Water | 60.0 g |
|  | Glycerol | 1.92 g |
| (C) | Preservative | 0.19 g |
|  | Water | 17.08 g |
| (D) | Triethanolamine | 0.77 g |
| (E) | Cyclopentadimethylsiloxane | 15.36 g |

The charged and coated microspheres (A) are dispersed in (B) at ambient temperature. Phase (C), previously heated to 80° C. and neutralized with triethanolamine (D) is then added. The volatile silicone (E) is dispersed last at ambient temperature.

A composition is obtained in which the dispersion of the charged and coated microspheres is perfectly homogenous. Moreover, the presence in this composition of perfluoropolymethylisopropyl ether (FOMBLIN HC25) in the form of the coating for the charged microspheres, imparts to the composition a very agreeable touch, particularly at the level of smoothness and good spreading properties.

EXAMPLE 20

Cheek makeup

| Charged and coated poly β-alanine microspheres obtained according to Example 4 | 4 g |
|---|---|
| Paraffin oil | 54.25 g |
| Petrolatum oil | 11.20 g |
| Carnauba wax | 5.60 g |
| Polyethylene wax | 5.60 g |
| Mica titanium | 11.20 g |
| Titanium dioxide | 5.60 g |
| D&C Red No. 7 | 0.20 g |
| Iron oxide | 2.20 g |
| Propylparahydroxybenzoate | 0.10 g |
| Butylhydroxytoluene | 0.05 g |

We claim:

1. Porous microspheres having fixed on the exterior surface thereof a coating of a substance not penetrating the interior of the pores of said microspheres, said coating consisting of a member selected from the group consisting of a perfluorinated oil, a fluorinated silicone oil and a silicone gum having the formula $$R-\underset{\underset{CH_3}{|}}{\overset{\overset{CH_3}{|}}{Si}}-O-\left[\underset{\underset{CH_3}{|}}{\overset{\overset{R'}{|}}{Si}}-O\right]_n-\underset{\underset{CH_3}{|}}{\overset{\overset{CH_3}{|}}{Si}}-R$$

wherein
R represents —CH$_3$, OH or —CH=CH$_2$,
R' represents —CH$_3$ or —C$_6$H$_5$ and
n is such that said silicone gum has a viscosity greater than $1 \times 10^{-2}$ m$^2$/s at 25° C.

2. The porous microspheres of claim 1 having an average particle size lower than 800 μm.

3. The porous microspheres of claim 1 selected from the group consisting of crosslinked poly β-alanine, polyacrylate, polyamide, polymethacrylate, polyethylene, polypropylene, styrene-divinyl benzyl copolymer, cellulose, silicone, silica and hydroxyapatite powder microspheres.

4. The porous microspheres of claim 1 wherein said coating comprises from 0.1 to 500 weight percent of said at least one of a perfluorinated oil, fluorinated silicone oil or silicone gum relative to the weight of said porous microspheres.

5. The porous microspheres of claim 1 wherein said perfluorinated oil is a perfluoroalkane having the formula C$_n$F$_{2n+2}$ wherein n is greater than 19.

6. The porous microspheres of claim 1 wherein said perfluorinated oil is a perfluoropolyether selected from the group consisting of (a) a perfluoropolyether having the formula $$CF_3O(\overset{\overset{CF_3}{|}}{CF}-CF_2O)_m(CF_2O)_n-CF_3,$$

wherein the ratio m/n is 5 to 40, (b) a perfluoropolyether having the formula $$RCF_2O-(C_2F_4O)_p(CF_2O)_q-CF_2R,$$

wherein the ratio p/q is 0.5 to 1.5, R represents fluorine, —COOH, —COOCH$_3$, —CH$_2$OH, —CH$_2$O—CH$_2$—CHOH—CH$_2$OH or —CH$_2$(OCH$_2$CH$_2$)$_p$—OH wherein p is 1 or 2, (c) a perfluoropolyether having the formula $$F-(\overset{\overset{CF_3}{|}}{CF}-CF_2O)_n C_2F_5,$$

wherein n is 10–500, and (d) a perfluoropolyether having the formula $$CF_3-CF-O-(CF_2-\overset{\overset{CF_3}{|}}{CF}-O)_m C_3F_7,$$
$$CF_3-\underset{\underset{CF_3}{|}}{CF}-O-(CF_2-CF-O)_n C_3F_7$$

wherein m and n are whole numbers ranging from 0 to 3, such that the molecular weight of said perfluoropolyether (d) is greater than 1,000.

7. The porous microspheres of claim 1 wherein said fluorinated silicone oil is selected from the group consisting of (a) a fluorinated silicone oil having the formula $$CH_3-\underset{\underset{CH_3}{|}}{\overset{\overset{CH_3}{|}}{Si}}-O-\left[\underset{\underset{(CH_2)_p-RF}{|}}{\overset{\overset{CH_3}{|}}{Si}}-O\right]_n\left[\underset{\underset{CH_3}{|}}{\overset{\overset{CH_3}{|}}{Si}}-O\right]_m-\underset{\underset{CH_3}{|}}{\overset{\overset{CH_3}{|}}{Si}}-CH_3$$

wherein
n is a whole number ranging from 1 to 300,
m is a whole number ranging from 0 to 150, p is a whole number ranging from 0 to 5, and
RF is a perfluoroalkyl radical having from 1 to 8 carbon atoms, and (b) a fluorinated silicone oil having the formula

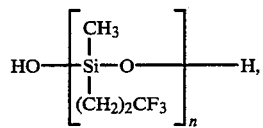

wherein n is greater than 3.

8. A cosmetic composition comprising in a cosmetically acceptable vehicle the porous microspheres of claim 1.

9. The cosmetic composition of claim 8 wherein said porous microspheres are present in an amount ranging from 0.1 to 60 weight percent.

10. The porous microspheres of claim 1 having an average particle size ranging from 0.1 to 300 µm.

11. Microspheres having fixed on the exterior surface thereof a coating consisting of a member selected from the group consisting of a perfluorinated oil, a fluorinated silicone oil and a silicone gum having the formula

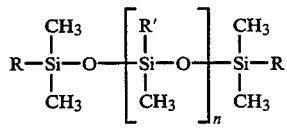

wherein
R represents —$CH_3$, OH or —$CH=CH_2$,
R' represents —$CH_3$ or —$C_6H_5$ and
n is such that said silicone gum has a viscosity greater than $1 \times 10^{-2} m^2/s$ at 25° C., the pores of said microspheres being charged with a hydrophilic, lipophilic or perfluorinated phase.

12. The microspheres of claim 1 wherein said hydrophilic phase is water, a polyhydroxyl alcohol or a mixture of water and a polyhydroxyl alcohol.

13. The microspheres of claim 12 wherein said polyhydroxyl alcohol is selected from the group consisting of glycerol and 1,2-propanediol.

14. The microspheres of claim 11 wherein said hydrophilic phase contains at least one water soluble active component selected from the group consisting of D-panthenol, glyceryl polymethacrylate, sodium hyaluronate, the sodium salt of pyroglutamic acid and a vitamin.

15. The microspheres of claim 11 wherein said lipophilic phase is paraffin oil, jojoba oil, ricin oil, squalene, isopropyl myristate or silicone oil.

16. The microspheres of claim 15 wherein said lipophilic phase contains at least one liposoluble active component selected from the group consisting of α-tocopherol acetate, tocopherol nicotinate, β-carotene, N,N-diethyltoluamide, a liposoluble U.V. filter, zinc ricinoleate, an antioxidant and a preservative.

17. The microspheres of claim 11 wherein said perfluorinated phase is a perfluoroalkane or a perfluoropolyether having a molecular weight less than 1,000.

18. A cosmetic composition comprising in a cosmetically acceptable vehicle the microspheres of claim 11.

19. The cosmetic composition of claim 18 wherein said microspheres are present in an amount ranging from 0.1 to 60 weight percent.

* * * * *